United States Patent
Balabanian et al.

(10) Patent No.: US 12,129,487 B2
(45) Date of Patent: Oct. 29, 2024

(54) METHOD TO OBTAIN LYMPHOID PROGENITORS

(71) Applicants: INSERM (Institute National de la Santé et de la Recherche Médicale), Paris (FR); Université Paris-Sud, Orsay (FR)

(72) Inventors: Karl Balabanian, Clamart (FR); Christelle Freitas, Clamart (FR); Vincent Rondeau, Clamart (FR)

(73) Assignees: INSERM (INSTITUT NATIONAL DE LA SANTÉ ET DE LA RECHERCHE MÉDICALE), Paris (FR); UNIVERSITÉ PARIS-SUD, Orsay (FR)

( * ) Notice: Subject to any disclaimer, the term of this patent is extended or adjusted under 35 U.S.C. 154(b) by 689 days.

(21) Appl. No.: 16/498,803

(22) PCT Filed: Mar. 26, 2018

(86) PCT No.: PCT/EP2018/057580
§ 371 (c)(1),
(2) Date: Sep. 27, 2019

(87) PCT Pub. No.: WO2018/177971
PCT Pub. Date: Oct. 4, 2018

(65) Prior Publication Data
US 2020/0048610 A1 Feb. 13, 2020

(30) Foreign Application Priority Data
Mar. 27, 2017 (EP) ..................... 17305344

(51) Int. Cl.
*C12N 5/0789* (2010.01)
*C12N 5/00* (2006.01)

(52) U.S. Cl.
CPC ......... *C12N 5/0647* (2013.01); *C12N 5/0018* (2013.01); *C12N 2501/21* (2013.01); *C12N 2501/2303* (2013.01); *C12N 2501/2306* (2013.01); *C12N 2501/2307* (2013.01); *C12N 2501/26* (2013.01)

(58) Field of Classification Search
None
See application file for complete search history.

(56) References Cited

U.S. PATENT DOCUMENTS

| | | | | |
|---|---|---|---|---|
| 7,399,633 | B2* | 7/2008 | Bernstein | A61P 43/00 435/372 |
| 2007/0026520 | A1* | 2/2007 | Kelly | C12N 5/0611 435/366 |
| 2015/0164952 | A1* | 6/2015 | Mahmud | G01N 33/5023 435/377 |
| 2015/0225697 | A1* | 8/2015 | Law | C12N 5/0646 435/372 |
| 2016/0251622 | A1* | 9/2016 | Sandler | A61P 35/02 424/93.7 |
| 2016/0298084 | A1* | 10/2016 | Heidaran | C12N 5/0605 |
| 2018/0110832 | A1* | 4/2018 | Morrison | A61K 38/29 |
| 2020/0268722 | A1* | 8/2020 | Racioppi | A61K 31/4745 |
| 2020/0392533 | A1* | 12/2020 | Wagers | A61P 7/00 |
| 2021/0008109 | A1* | 1/2021 | Kang | A61K 39/0011 |
| 2022/0259563 | A1* | 8/2022 | Hariri | A61P 35/04 |
| 2024/0041933 | A1* | 2/2024 | Delaney | A61K 35/28 |

FOREIGN PATENT DOCUMENTS

WO 2016/123100 A1 8/2016

OTHER PUBLICATIONS

Nguyen et al., Stem Cells, 2015, v.33 pp. 2838-2849.*
Frisz et al ( Analytical Chemistry, 2012,v,84, p. 4307-4313.*
Mirshafiee et al., ( Tissue Engineering, 2018, v.24, p. 322-330.*
Minami et al., J of Immunol, 2017, v. 199, pp. 2343-2355.*
Dravid et al.; "Dysregulated Gene Expression During Hematopoietic Differentiation From Human Embryonic Stem Cells"; Molecular Therapy, vol. 19, No. 4, Apr. 1, 2011, pp. 768-781.
Vodyanik et al.; "Human embryonic stem cell-derived CD34+ cells: efficient production in the coculture with OP9 stromal cells and analysis of lymphohematopoietic potential"; Blood, vol. 105, No. 2, Jan. 15, 2005, pp. 617-626.
Sobkow et al.; "Prolonged transendothelial migration of human haematopoietic stem and progenitor cells (HSPCs) towards hydrogel-released SDF1"; Annals of Hematology, vol. 90, No. 8, Jan. 20, 2011, pp. 865-871.
Balabanian et al.; "Hematopoieses and Stem Cells: Proper desensitization of CXCR4 is required for lymphocyte development and peripheral compartimentalization in mice"; Blood Journal, vol. 119, No. 24, Jun. 14, 2012, pp. 5722-5730.
Doulatov et al.; "Hematopoiesis: A Human Perspective"; Cell Stem Cell, vol. 10, No. 2, pp. 120-136.

* cited by examiner

*Primary Examiner* — Michail A Belyavskyi
(74) *Attorney, Agent, or Firm* — WC&F IP

(57) ABSTRACT

The present invention relates to a method for preparing lymphoid progenitors. The inventors took advantage of their original and relevant Warts, Hypogammaglobulinemia, Infections and Myelokathexis (WHIM) Syndrome (WS) model and the access to blood samples from five WS patients to investigate the impact of CXCR4 desensitization on BM and extra-medullary (i.e. splenic) hematopoiesis and hematopoietic stem and progenitor cells (HSPCs) recirculation. They developed, for the first time, an original in vitro system permitting to selectively expand HSPCs to obtain lymphoid progenitors by using an original cocktail of cytokines. In particular, the present invention relates to an in vitro method for preparing lymphoid progenitors by culturing HSPCs in an appropriate culture medium comprising an effective amount of a cocktail of cytokines consisting in SCF, IL-3, IL-6, IL-7, Flt-3, and CXCL12.

2 Claims, 3 Drawing Sheets

METHOD TO OBTAIN LYMPHOID PROGENITORS

FIELD OF THE INVENTION

Figure 1:
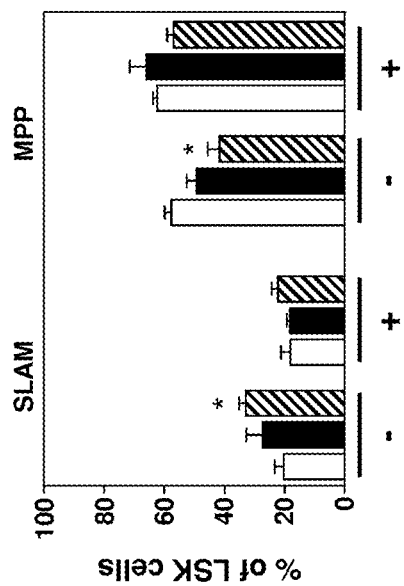
Figure 1:
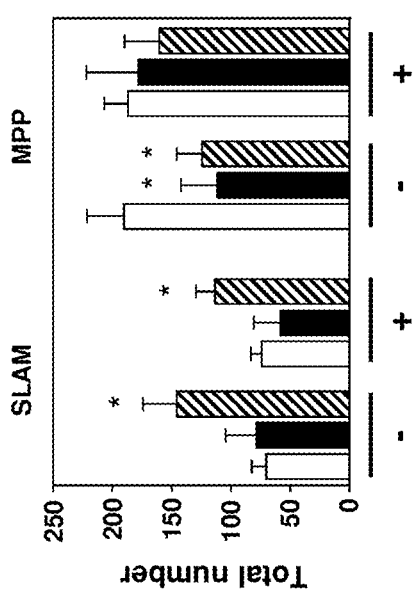
Figure 1:
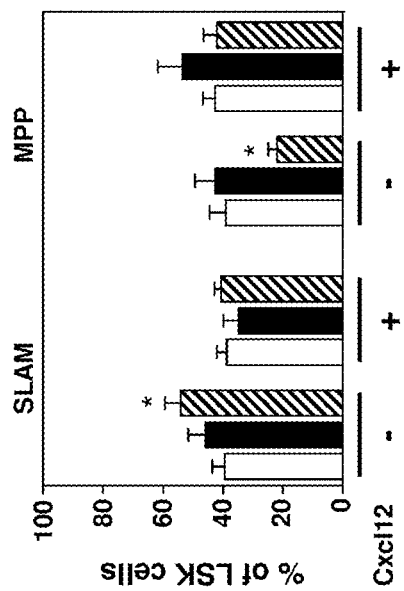
Figure 1:
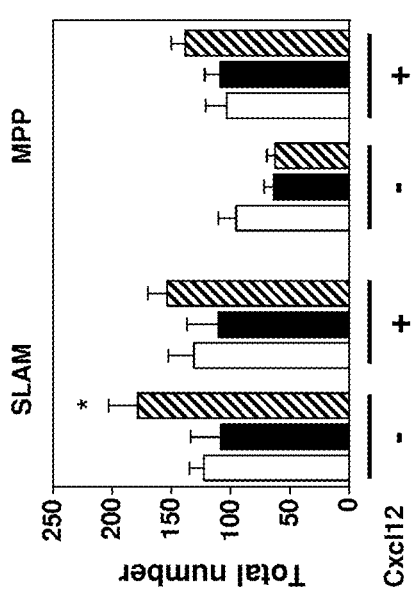

The present invention relates to an in vitro method for preparing lymphoid progenitors, said method comprising the step of culturing hematopoietic stem and progenitor cells (HSPCs) in an appropriate culture medium comprising an effective amount of a cocktail of cytokine selected in the group consisting in SCF, IL-3, IL-6, IL-7 and Flt-3.

BACKGROUND OF THE INVENTION

CXCR4 is a broadly expressed G-protein-coupled receptor whose activation by its natural ligand, the CXC α-chemokine Stromal cell-derived factor-1 (SDF-1/CXCL12), is essential for organogenesis and critically involved in fetal B-cell lymphopoiesis and bone marrow (BM) myelopoiesis (Ma et al., 1998; Nagasawa et al., 1998, 1996). In postnatal life, CXCR4 mediates the engraftment, retention and multilineage differentiation of hematopoietic stem and progenitor cells (HSPCs) in various CXCL12-expressing niches in the BM by regulating their migration, survival and quiescence (Karpova and Bonig, 2015; Peled et al., 1999; Foudi et al., 2006; Nie et al., 2008; Cordeiro Gomes et al., 2016). This signaling axis is also involved at different stages in the production and distribution of B-, T-, and myeloid cells in lymphoid organs (LO) and peripheral blood (Nagasawa et al., 1996; Scimone et al., 2004; Eash et al., 2010; Onai et al., 2000; Kawabata et al., 1999). Our current understanding of the role of CXCR4 in lymphocyte biology is mostly based on data generated from mice deficient in Cxcr4, Cxcr4$^{-/-}$ BM chimeras or conditional knock-out mice in which Cxcr4 was selectively inactivated in the B- or T-cell lineage (Nagasawa et al., 1996; Ma et al., 1998; Nagasawa et al., 1998; Nie et al., 2008; Trampont et al., 2010; Tzeng et al., 2011). More recently, selective ablation of Cxcl12 or Cxcr4 in BM stroma has allowed the identification of specialized niches supporting the maintenance of HSPCs and leukemia-initiating cells (Ding and Morrison, 2013; Pitt et al., 2015; Itkin et al., 2016).

During the last decade, our understanding of the crucial roles played by CXCR4 desensitization and endocytosis in regulating its signaling pathways and activities has grown substantially. Upon CXCL12 exposure, β-arrestins are recruited to the carboxyl-terminal tail (C-tail) domain of the receptor, precluding further G-protein activation (i.e. desensitization) and leading to receptor internalization. Moreover, CXCR4 internalization is associated with HSPCs entry into the circulation (Christopher et al., 2009). In line with this, in normal human circulating CD34$^+$ hematopoietic progenitor cells (HPCs), a large proportion of CXCR4 is sequestered intracellularly as a consequence of constitutive internalization (Zhang et al., 2004). Together, this suggests that the intracellular trafficking of CXCR4 is a highly regulated process and raises the question as to their role in the biological properties of HSPCs. Dysregulated CXCR4 inactivation and internalization might be expected to impair HSPC differentiation, recirculation or trafficking, resulting in cytopenia and immunodeficiency.

The majority of cases of the rare combined primary immunodeficiency Warts, Hypogammaglobulinemia, Infections and Myelokathexis (WHIM) Syndrome (WS) have been linked to inherited autosomal dominant gain-of-function mutations in CXCR4 (Dotta et al., 2011; Kawai and Malech, 2009). These result in the distal truncation of the C-tail of CXCR4 and a desensitization- and internalization-resistant receptor in response to CXCL12 (Hernandez et al., 2003; Balabanian et al., 2005). Patients also exhibit a severe, chronic pan-leukopenia with naive T cells and mature recirculating B cells being most affected (Gulino et al., 2004). Given that CXCR4 is widely expressed on non-hematopoietic cells and virtually on all leukocytes at multiple stages of development, one possibility could be that the WS-associated peripheral blood leukopenia is a consequence of skewed production, differentiation or distribution of leukocytes related to altered CXCR4-mediated signaling. The recent discovery by McDermott and collaborators of a chromothriptic cure of the WS supports this hypothesis (McDermott et al., 2015). They found deletions of one copy of chromosome 2, including the disease allele CXCR4$^{R334X}$, in a hematopoietic stem cell (HSC) of a patient who had spontaneously repopulated the myeloid but not the lymphoid lineage. This natural experiment strongly suggests that WS-related neutropenia and monocytopenia stem from a hematopoietic defect. However, these findings still leave the mechanisms underpinning T- and B-cell lymphopenia to be elucidated.

Recently, the inventors have been able to replicate the hematologic phenotype of WS using a knock-in Cxcr4$^{+/1013}$ mouse strain (+/1013) that harbors the WS-linked heterozygous CXCR4$^{S338X}$ mutation causing a distal truncation of the last 15 residues of the C-tail domain (Balabanian et al., 2012). Indeed mutant mice displayed in vitro lymphocytes with enhanced migration to Cxcl12 and phenocopied severe lymphopenia. First-line analyses of +/1013 mice suggested developmental defects at the pro/pre-B cell stage in the BM and during the early double-negative (DN) stages of thymocyte maturation as causative in the decreased peripheral B- and T-cell numbers (Balabanian et al., 2012). However, whether impaired lymphopoiesis stems from an upstream cell-intrinsic hematopoietic defect remains to be established.

SUMMARY OF THE INVENTION

The inventors took advantage of their original and relevant knock-in mouse model and the access to blood samples from five WS patients to investigate the impact of CXCR4 desensitization on BM and extra-medullary (i.e. splenic) hematopoiesis and hematopoietic stem and progenitor cell (HSPC) recirculation. They developed, for the first time, an original in vitro system permitting to selectively expand HSPCs to obtain lymphoid progenitors by using an original cocktail of cytokines.

Thus, the present invention relates to an in vitro method for preparing lymphoid progenitors, said method comprising the step of culturing HSPCs in an appropriate culture medium comprising an effective amount of a cocktail of cytokine selected in the group consisting in SCF, IL-3, IL-6, IL-7 and Flt-3. Particularly, the invention is defined by the claims.

DETAILED DESCRIPTION OF THE INVENTION

Thus the present invention relates to an in vitro method for preparing lymphoid progenitors, said method comprising the step of culturing hematopoietic stem and progenitor cells (HSPCs) in an appropriate culture medium comprising an effective amount of a cocktail of cytokines selected in the group consisting in SCF, IL-3, IL-6, IL-7 and Flt-3.

In one embodiment, the invention relates to an in vitro method for preparing lymphoid progenitors, said method comprising the step of culturing hematopoietic stem and progenitor cells (HSPCs) in an appropriate culture medium comprising an effective amount of a cocktail of cytokines consisting in SCF, IL-3, IL-6, IL-7 and Flt-3. In other words, the culture medium comprises the 5 cytokines SCF, IL-3, IL-6, IL-7 and Flt-3.

In one embodiment, the lymphoid progenitors may be MLP (Immature Multi-Lymphoid Progenitors) for the human lineage or LMPP (Lymphoid-Primed Multipotential Progenitors) for the mouse lineage.

Thus, the invention also relates to an in vitro method for preparing MLP or LMPP, said method comprising the step of culturing HSPCs in an appropriate culture medium comprising an effective amount of a cocktail of cytokines consisting in SCF, IL-3, IL-6, IL-7 and Flt-3.

As used herein, the term "HSPCs" for "Haematopoietic Stem and Progenitor Cells" has its general meaning in the art. According to the invention, for human lineage, HSPC denotes HSC (Human Stem Cells (HSCs)) and progenitors and are Lin$^-$, CD34$^+$ and HSCs are Lin$^-$, CD34$^+$, CD38$^-$, CD45RA$^-$, CD90$^+$, CD49 f$^+$. According to the invention, for mouse lineage, HSPC denotes LSK SLAM, MPP, LMPP, CLP, ProB, ETP and myeloid progenitors (CMP, GMP et MEP). LSK SLAM for "Signaling Lymphocyte Activation Molecule" are Lin$^-$c-Kit$^+$Sca-1$^+$(LSK) CD48$^-$CD150$^+$. For human and mouse lineage, HSPCs are the stem cells and progenitors that give rise to all the other blood cells through the process of haematopoiesis. They are derived from mesoderm and located in the red BM, which is contained in the core of most bones (see Doulatov et al., 2012).

Thus, in another embodiment, the invention also relates to an in vitro method for preparing lymphoid progenitors, said method comprising the step of culturing HSCs in an appropriate culture medium comprising an effective amount of a cocktail of cytokines selected in the group consisting in SCF, IL-3, IL-6, IL-7 and Flt-3.

In a particular embodiment, the invention relates to an in vitro method for preparing lymphoid progenitors, said method comprising the step of culturing HSCs in an appropriate culture medium comprising an effective amount of a cocktail of cytokines consisting in SCF, IL-3, IL-6, IL-7 and Flt-3.

As used herein the term "MLP" for "Immature Multi-Lymphoid Progenitors" has its general meaning in the art. This term is used for human lineage. MLP characterized as CD34$^+$, CD45RA$^+$, CD10$^+$ and CD7$^-$ denotes cells derived from MPP and which give the lymphoid lineage (T-cells, B-cells and Natural Killer (NK) cells) (see Doulatov et al., 2012).

As used herein, the term "LMPP" for "Lymphoid Primed Multipotent Progenitor" has its general meaning in the art. This term is used for mouse lineage. LMPP characterized as LSK CD34$^+$Flt3$^{high}$ denotes cells derived from MPP and which give the lymphoid lineage (like CLP) and thus T-cells, B-cells and Natural Killer (NK) cells (see Doulatov et al., 2012).

As used herein, the term "MPP2" for "Multipotent Progenitor 2" has its general meaning in the art. This term is used for mouse lineage. MPP2 characterized as LSK CD48$^+$CD150$^+$Flt3$^-$ denotes cells derived from HSC and which display a megakaryocyte/erythroid (MegE)-biased differentiation potential (see Pietras et al., 2015).

As used herein, the term "MPP3" for "Multipotent Progenitor 3" has its general meaning in the art. This term is used for mouse lineage. MPP3 characterized as LSK CD48$^+$CD150$^-$Flt3$^-$denotes cells derived from HSC and which display a granulocyte/macrophage (GM)-biased differentiation potential (see Pietras et al., 2015).

As used herein, the term "MPP4" for "Multipotent Progenitor 4" has its general meaning in the art. This term is used for mouse lineage. MPP4 characterized as LSK CD48$^{+/-}$CD150$^-$Flt3$^+$ denotes cells derived from HSC and which display a lymphoid-biased differentiation potential (see Pietras et al., 2015). Note that this population overlaps with another lymphoid-biased progenitor definition based on reporter gene combinations and different surface markers, the LMPP population (see Doulatov et al., 2012). According to the invention and according to some nomenclatures (see Pietras et al., 2015 for example), LMPP and MPP4 could correspond to the same population of cells.

As used herein, the term "SCF" for "Stem Cell Factor" has its general meaning in the art. SCF denotes a hematopoietic growth factor and ligand for the KIT tyrosine kinase receptor, which exerts its activity in the early stages of haematopoiesis. SCF stimulates the proliferation of myeloid and erythroid in BM cultures. According to the invention, mSCF (mouse SCF) or hSCF (human SCF) can be used in the method of the invention.

As used herein, the term "IL-3" for "Interleukin-3" has its general meaning in the art. IL-3 denotes a protein that can improve the body's natural response to disease as part of the immune system. IL-3 stimulates the differentiation of HSPCs into myeloid progenitor cells or, with the addition of IL-7, into lymphoid progenitor cells. According to the invention, mIL3 (mouse IL-3) or hIL3 (human IL-3) can be used in the method of the invention.

As used herein, the term "IL-6" for "Interleukin-6" has its general meaning in the art. IL-6 is secreted by T cells and macrophages to stimulate immune response. IL-6 is an important mediator of fever and of the acute phase response. It is capable of crossing the blood-brain barrier and initiating synthesis of PGE2 in the hypothalamus, thereby changing the body's temperature set-point. According to the invention, mIL6 (mouse IL-6) or hIL6 (human IL-6) can be used in the method of the invention.

As used herein, the term "IL-7" for "Interleukin-7" has its general meaning in the art. IL-7 is a haematopoietic growth factor secreted by stromal cells in the BM and thymus. It is also produced by keratinocytes, dendritic cells, hepatocytes, neurons, and epithelial cells but is not produced by normal lymphocytes. IL-7 stimulates the differentiation of HSPCs into lymphoid progenitor cells. According to the invention, mIL7 (mouse IL7) or hIL7 (human IL7) can be used in the method of the invention.

As used herein, the term "FLT3" for "Fms-like tyrosine kinase 3" also known as "CD135" has its general meaning in the art. FLT3 denotes a cytokine receptor, which belongs to the receptor tyrosine kinase class III. It is expressed on the surface of many HPCs. Signaling of FLT3 is important for the normal development of HSPCs. According to the invention, mFLT3 (mouse FLT3) or hFLT3 (human FLT3) can be used in the method of the invention. As shown in the examples, ligand of FLT3 is used for the method of the invention. Thus, the term "cytokine FLT3" denotes the ligand of the FTL3 receptor (FLT-3L).

Thus, the invention also relates to an in vitro method for preparing lymphoid progenitors, said method comprising the step of culturing HSCs in an appropriate culture medium comprising an effective amount of a cocktail of cytokines selected in the group consisting in SCF, IL-3, IL-6, IL-7 and Flt-3L.

Thus, the invention also relates to an in vitro method for preparing lymphoid progenitors, said method comprising the step of culturing HSCs in an appropriate culture medium comprising an effective amount of a cocktail of cytokines consisting in SCF, IL-3, IL-6, IL-7 and Flt-3L.

As used herein, the term "FLT-3L" for "Fms-like tyrosine kinase 3 ligand" has its general meaning in the art. FLT-3L denotes a cytokine which combined with other cytokines can stimulate the proliferation and differentiation of various blood cell progenitors.

In one embodiment, the present invention also relates to an in vitro method for preparing lymphoid progenitors, said method comprising the step of culturing HSPCs in an appropriate culture medium comprising an effective amount of a cocktail of cytokines selected in the group consisting in mSCF, mIL-3, hIL-6, mIL-7 and hFlt-3.

In another embodiment, the present invention also relates to an in vitro method for preparing lymphoid progenitors, said method comprising the step of culturing HSPCs in an appropriate culture medium comprising an effective amount of a cocktail of cytokines consisting in mSCF, mIL-3, hIL-6, mIL-7 and hFlt-3.

In one embodiment, a step of isolating lymphoid progenitors is added at the end of the methods described above.

In another embodiment, the culture medium also comprises an effective amount of the chemokine CXCL12.

As used herein, the term "CXCL12" for "C—X—C motif chemokine 12" has its general meaning in the art. CXCL12 or Stromal cell derived factor-1 (SDF-1) is strongly chemotactic for lymphocytes. During embryogenesis it directs the migration of haematopoietic cells from foetal liver to BM and the formation of large blood vessels.

Thus, in a particular embodiment, the invention relates to an in vitro method for preparing lymphoid progenitors, said method comprising the step of culturing HSPCs in an appropriate culture medium comprising an effective amount of a cocktail of cytokines consisting in SCF, IL-3, IL-6, IL-7, Flt-3 and CXCL12. In other words, the culture medium comprises the 6 cytokines SCF, IL-3, IL-6, IL-7, Flt-3 and CXCL12.

It is noted that, according to the invention, the term FLt-3 used corresponds to the Flt-3L (ligand of Flt-3).

In a particular embodiment, the culture medium may comprises or not a feeder.

In a particular embodiment, the culture medium does not comprise a feeder.

As used herein, the term "feeders" has its general meaning in the art. Feeders denote cells used in co-culture techniques, which support the growth of the other cells in the culture. Feeder cells provide auxiliary substances including attachment substrates, nutrients, or other factors that are needed for growth in culture. Generally, feeders are fibroblasts, mouse embryonic fibroblasts (MEFs) or stromal cell lines (e.g., ST2, MS5, PA6, OP9 or OP9-DL1).

Typically, the feeder cells are adherent cells and are cultured in appropriate culture system such as plates or dishes, so that the feeder cells form a layer. Culture conditions may vary, but standard tissue culture conditions form the basis of the co-culture. Typically, cells are incubated in 5% CO2 incubators at 37° C. in a culture medium.

In one embodiment, for mouse lineage, HSCs are differentiated at first in MPPs and then in lymphoid progenitors (see Doulatov et al., 2012).

In another particular embodiment, for mouse lineage, the LMPPs are, in a next step, differentiated in CLPs (see Doulatov et al., 2012).

In another particular embodiment, for mouse lineage, the MPP4 are, in a next step, differentiated in CLPs (see Pietras et al., 2015).

As used herein, the term "MPP" for "Multipotent Progenitor" has its general meaning in the art. MPP described as LSKCD48$^-$CD150$^-$ (for mouse lineage) constitute a biological cell that, like a stem cell, has the capacity to differentiate into all blood cells, but is already more specific than a stem cell and is pushed to differentiate into its "target" cell. The most important difference between stem cells and progenitor cells is the self-renewal ability that have stem cells and not progenitor cells (see Doulatov et al., 2012). Note that according to some nomenclatures, this population could overlap with another hematopoietic stem cell definition based on reporter gene combinations and different surface markers, the short-term HSC population (see Pietras et al., 2015).

As used herein, the term "CLP" for "Common Lymphoid Progenitor" has its general meaning in the art and is used for mouse lineage. CLP defined as Lin$^-$c-Kit$^{low}$Sca-1$^{low}$CD127$^+$Flt3$^+$ are committed lymphoid progenitor cells, and give rise to T-lineage cells, B-lineage cells and NK cells.

As used herein, the term "culture medium" refers to a chemical composition that supports the growth and/or differentiation of a cell, suitably of a mammalian cell. Typical culture media include suitable nutrients (e.g. sugars, amino acids, proteins, and the like) to support the growth and/or differentiation of a cell. Media for the culture of mammalian cells are well known to those of skill in the art and include, but are not limited to Medium 199, Eagle's Basal Medium (BME), Eagle's Minimum Essential Medium (MEM), alpha modification MEM (MEM), Minimum Essential Medium with Non-Essential Amino Acids (MEM/NEAA), Dulbecco's Modification of Eagle's Medium (DMEM), McCoy's 5 A, Rosewell Park Memorial Institute (RPMI) 1640, modified McCoy's 5 A, Ham's F10 and F 12, CMRL 1066 and CMRL 1969, Fisher's medium, Glasgow Minimum Essential Medium (GMEM), Iscove's Modified Dulbecco's Medium (IMDM), Leibovitz's L-15 Medium, McCoy's 5A medium, S-MEM, NCTC-109, NCTC-135, Waymouth's MB 752/1 medium, Williams' Medium E, and the like.

In one embodiment, the culture medium comprises between 5% to 20% of Fetal Bovine Serum (FBS), more particularly between 8% to 12%.

In one embodiment, the culture medium comprises between 0.2% to 5% of penicillin more particularly between 0.5% to 2%.

In one embodiment, the culture medium comprises between 1 to 100 ng/ml of the cytokines of the invention (SCF, IL-3, IL-6, IL-7 and Flt3), more particularly between 5 and 70 ng/ml. Particularly, the concentration of the cytokines of the invention may be 5, 10 or 50 ng/ml.

In one embodiment, the culture medium comprises between 1 to 1000 ng/ml of the CXCL12 cytokine of the invention, more particularly between 5 and 700 ng/ml. Particularly, the concentration of the cytokine of the invention may be 5, 10, 100 or 500 ng/ml.

Typically, in particular embodiment, HSPCs are cultured in DMEM medium supplemented with 10% FBS, 1% penicillin as well as the cytokines described above (SCF, IL-3, IL-6, IL-7 and Flt3) at 5, 10 or 50 ng/mL and 1 to 1000 ng/ml for CXCL12. Cytokines were added to the feeder-free medium at the start of the experiment only. Cells were harvested at different times to analyze HSPC differentiation by flow cytometry.

Typically, the duration of the culturing step is in the range of about 2 to 14 days, more particularly about 4 to 7 days. In some embodiments, the duration of the culturing step is 4, 5, 6 or 7 days.

In some embodiments, the method of the present invention involves culturing HSPCs that have been isolated, or partially purified, from cord blood. HSCs may be isolated from cord blood using any of the methods well known to persons skilled in the art. One preferred method involves the isolation of HSC from the fraction(s) of centrifuged cord blood, which remain following removal of erythrocytes, by magnetic bead-based methods such as the magnetically activated cell sorting (MACS) protocol described in the MicroBead Kit from Miltenyi Biotec (Miltenyi Biotec GmbH, Cologne, Germany (2006)).

In some embodiments, the population of HSCs was previously expanded in an appropriate culture medium before being cultured in the presence of the culture medium. The term "expansion" refers to growing cells in culture to achieve a larger homogenous population of the cells.

The method of the present invention is particularly suitable for the preparation of large amounts of lymphoid progenitors which can be subsequently used e.g. for research or therapeutics applications.

For example, the lymphoid progenitors obtained by the method of the invention may be used in a patient with a WS.

Thus, the invention also relates to a population of lymphoid progenitors obtained by the method of the invention for use in the treatment of a patient suffering of a WS.

As used herein, the term "WHIM Syndrome" has its general meaning in the art and denotes a rare congenital immunodeficiency disorder characterized by chronic non-cyclic neutropenia and lymphopenia.

In another embodiment, the invention also relates to a population of lymphoid progenitors obtained by the method of the invention for use to treat some myelodysplastic syndromes, for optimizing cell-based therapy or in BM graft context.

The invention will be further illustrated by the following figures and examples. However, these examples and figures should not be interpreted in any way as limiting the scope of the present invention.

FIGURES

FIG. 1: Equal numbers of purified LSK SLAM from the BM of WT (white bars), +/1013 (black bars) or 1013/1013 (hatched bars) mice were cultured for 4 days in a cytokine-supplemented feeder-free media in the presence or absence of CXCL12. Percentages and absolute numbers (mean±SEM, n=5) of LSK SLAM and MPPs were determined by flow cytometry after 2 and 4 days of culture. *$P<0.05$ compared with WT cells (as determined using the two-tailed Student's t-test).

Figure 2:
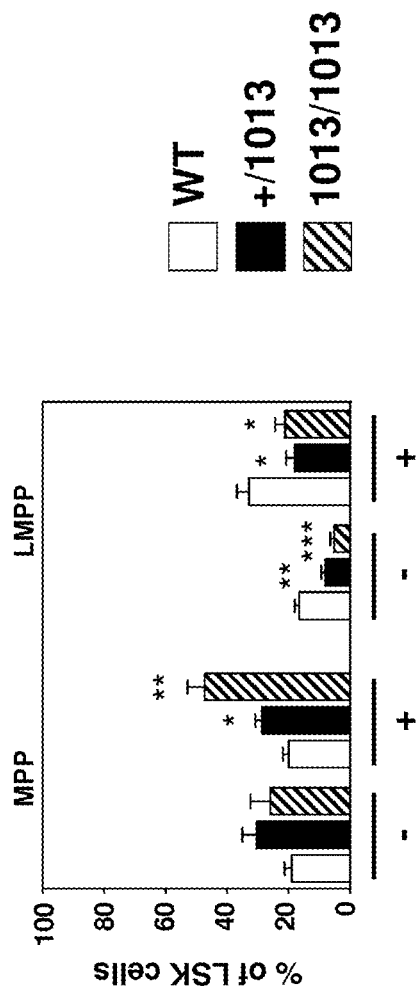
Figure 2:
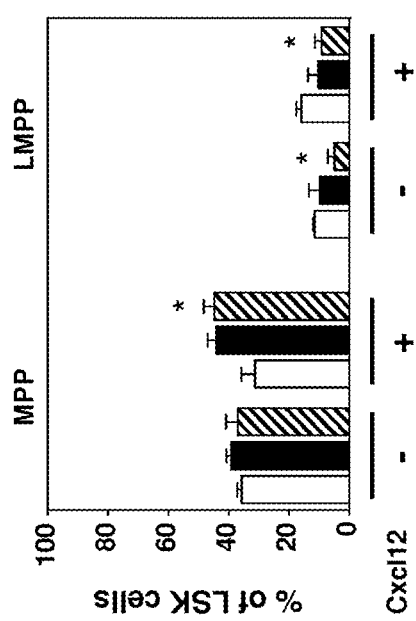
Figure 2:
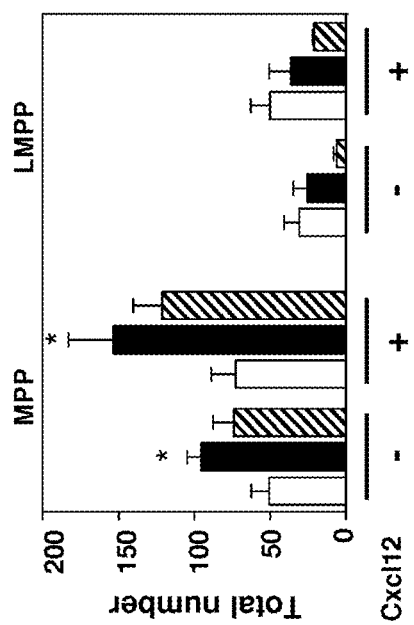
Figure 2:
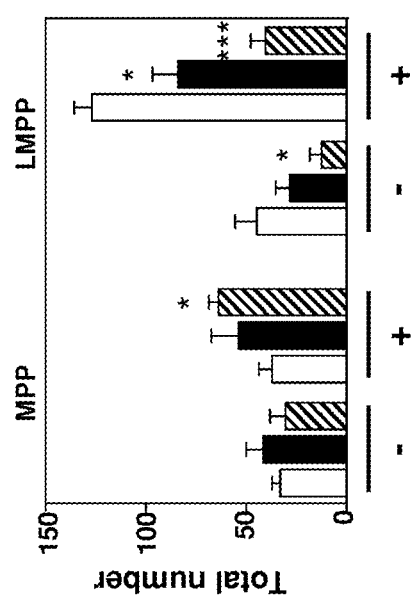

FIG. 2: Equal numbers of purified MPPs from the BM of WT (white bars), +/1013 (black bars) or 1013/1013 (hatched bars) mice were cultured for 4 days in a cytokine-supplemented feeder-free media in the presence or absence of CXCL12. Percentages and absolute numbers (mean±SEM, n=5) of MPPs and LMPPs were determined by flow cytometry after 2 and 4 days of culture. *$P<0.05$, $P<0.005$ and *$P<0.0005$ compared with WT cells (as determined using the two-tailed Student's t-test).

Figure 3:
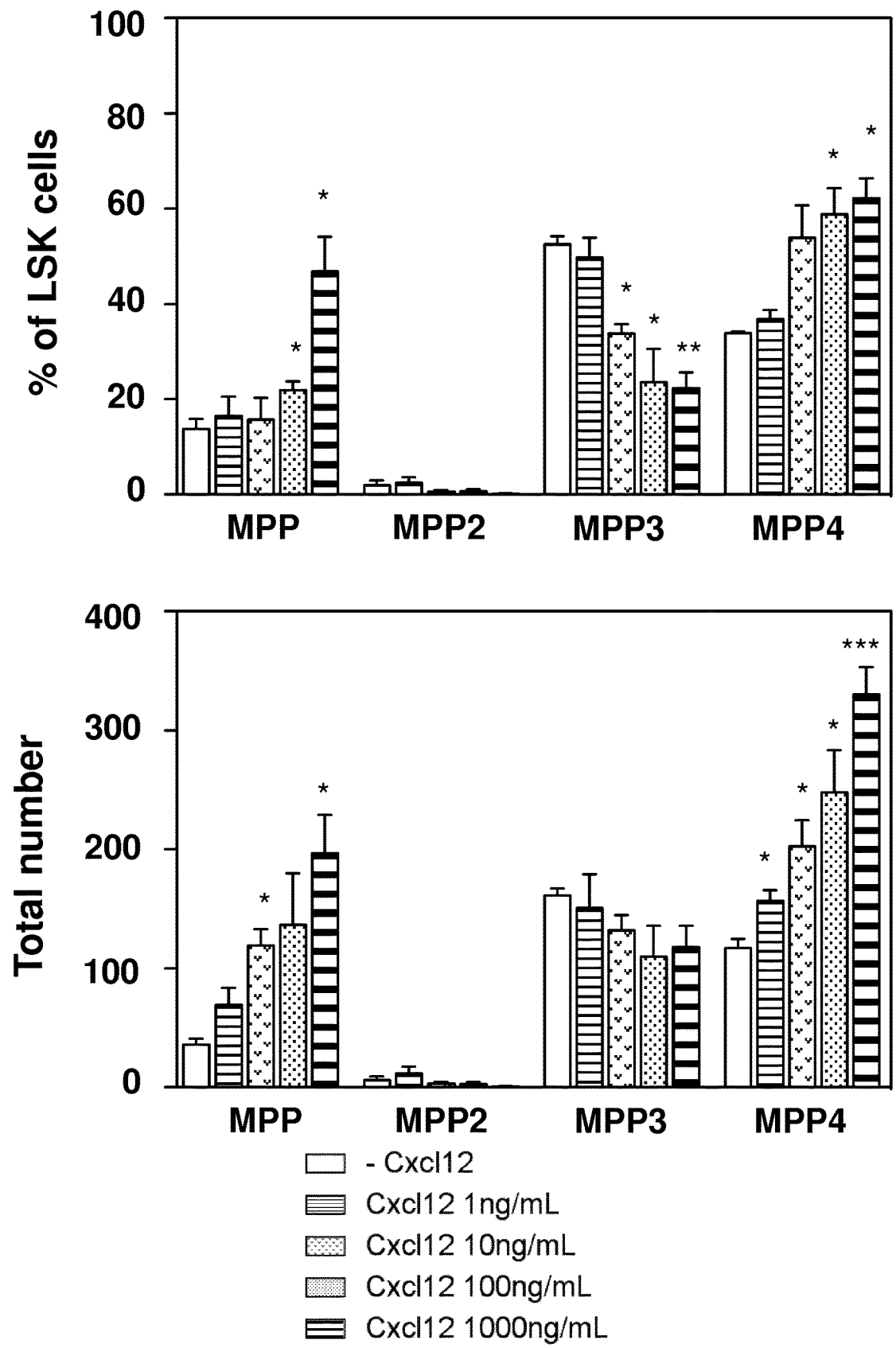

FIG. 3: Equal numbers of purified MPPs from the BM of WT mice were cultured for 4 days in a cytokine-supplemented feeder-free media in the presence or absence of different concentrations of CXCL12. Percentages and absolute numbers (mean±SEM, n=3) of MPPs, MPP2, MPP3 and MPP4 were determined by flow cytometry after 4 days of culture. *$P<0.05$, $P<0.005$ and *$P<0.0005$ compared with the culture without CXCL12 (as determined using the two-tailed Student's t-test).

EXAMPLES

Example 1: Whim Syndrome Model

Material & Methods

Patients and HSPC Analyses

All WS patients included in this study were registered in the French Severe Chronic Neutropenia Registry coordinated by Pr. J. Donadieu (Service d'Hématologie et Oncologie Pédiatrique, Trousseau Hospital, Paris). Investigations of blood samples were carried out in compliance with Good Clinical Practices and the Declaration of Helsinki. All individuals or parents for children have provided written informed consent prior to sampling, data registering and genetic analyses. Patients P1 (9-years old), P2 and P3 from the same family (41- and 9-years old respectively), P4 (11-years old) and P5 (29-years old) displayed clinical features of WS, including a marked leukopenia. At the time of the study, P1, P2, P3, P4 and P5 had a leukocyte count of $0.76 \times 10^9$/L, $1.07 \times 10^9$/L, $0.93 \times 10^9$/L, $0.85 \times 10^9$/L and $2.6 \times 10^9$/L respectively. Four of them had autosomal dominant mutations in CXCR4 (P1: c.1000C>T, p.Arg334*; P2 and P3: c.1013dup, p.Ser339Ilefs*5; and P4: c.1013C>G, p.Ser338*). P1 and P2 have been described previously (Beaussant Cohen et al., 2012), while P5 had a WT CXCR4 coding sequence (WHIM$^{WT}$) (Balabanian et al., 2005). Age- and sex-matched healthy blood donor volunteers were run in parallel and used as control subjects. Whole blood phenotyping of HSPCs was performed as follows. Briefly, 600 µL of blood were labelled for 30 min at 4° C. with a combination of the following conjugated mAbs: anti-human CD7 (clone M-T701, mouse IgG1), CD10 (clone HI10A, mouse IgG1), CD34 (clone 581, mouse IgG1), CD38 (clone HIT2, mouse IgG1) and CD45RA (clone HI100, mouse IgG2b). Abs were conjugated to Brilliant Violet (BV) 421, BV 605, FITC, APC and AF700, and were purchased from BD Biosciences. Corresponding isotype- and species-matched Abs were used as negative controls. Thereafter, red blood cells were lyzed with OptiLyse C® buffer (Beckman Coulter) for 15 min at room temperature in the dark. Cells were analyzed on an LSR II Fortessa flow cytometer (BD Biosciences). For functional analyses, blood cells (300 µL) were plated, after erythrocyte lysis with Ammonium-Chloride-Potassium (ACK) buffer, in 35-mm tissue culture dishes into growth factor supplemented methylcellulose medium (StemCell Technologies). After 2 weeks of incubation at 37° C. in 5% $CO_2$, CFU-Cs were enumerated under an inverted microscope.

Mice and Genotyping

Cxcr4$^{+/1013}$ (+/1013) mice were generated by a knock-in strategy and bred as described (Balabanian et al., 2012). Cxcr4$^{1013/1013}$ (1013/1013) mice were obtained by crossing heterozygous +/1013 mice. WT mice were used as control. All mice were littermates and age-matched (8-12- or 56-weeks old, referred as young or middle-aged respectively). Adult Boy/J (CD45.1), WT, +/1013 and 1013/1013 (C57Bl/6J background, CD45.2) mice were bred in our animal facility under 12-hours light/dark cycle, specific pathogen-free conditions and feed ad libidum. All experiments were performed in accordance with the European Union guide for the care and use of laboratory animals and has been reviewed and approved by an appropriate institutional review committee (C2EA-26, Animal Care and Use Committee, Villejuif, France).

Sample Isolation

BM cells were extracted by centrifugation from intact femurs and tibia, while spleens and thymus were gently mashed on a 70-μm nylon strainer to generate a single cell suspension. Cell collection was performed in PBS FCS 2% and filtered through a 70-μm nylon strainer. All cell numbers were standardized as total count per 2 legs, spleen or thymus unless specified. The peripheral blood was collected by cardiac puncture. Red blood cell lysis was performed using ACK buffer before staining. Cells harvested from tissues were either immunophenotyped immediately, incubated at 37° C. for 60 min in RPMI 20 mM HEPES BSA 0.5% (Euromedex) prior to chemokine receptor internalization studies or kept at 4° C. overnight in PBS FCS 30% for chemotaxis assays.

Transplantation Experiments and In Vivo Functional Assays

For BM transplantation experiments, $1.5 \times 10^6$ total BM cells from young CD45.2$^+$ WT, +/1013 or 1013/1013 mice were injected into lethally irradiated young CD45.1$^+$ WT recipient mice (two rounds of 5.5 Gy separated by 3 h). Chimerism was analyzed 16 weeks after reconstitution. Total BM from these mice was then transplanted into a second set of lethally irradiated young CD45.1$^+$ WT recipient mice (secondary transplantation). For reverse transplantation experiments, $1.5 \times 10^6$ total BM cells from CD45.1$^+$ WT mice were injected into lethally irradiated CD45.2$^+$ WT, +/1013 or 1013/1013 recipient mice. For in vivo homing assays, $50 \times 10^6$ cells from total BM of CD45.2$^+$ WT, +/1013 or 1013/1013 mice were injected into lethally irradiated CD45.1$^+$ WT recipient mice (two rounds of 5.5 Gy separated by 3 h). Eighteen hours after injection, BM and spleen from recipient mice were harvested and the homing pattern of CD45.2$^+$ Lin$^-$, LSK or LSK SLAM cells was evaluated by flow cytometry. 5-FU (InvivoGen) was injected intraperitoneally to mice at a dose of 150 mg/kg. PBS was used as control. Mice were sacrificed 3.5 days after injection and the BM was analyzed by flow cytometry. Mice were treated with AMD3100 (5 mg/kg, Sigma) or PBS via intraperitoneal injection. One hour later, peripheral blood was harvested, analyzed by flow cytometry and tested for CFU-C assays.

In Vitro Functional Assays

BM cells or splenocytes ($1 \times 10^5$) and blood cells (100 μL) after erythrocyte lysis were plated in duplicate in 35-mm tissue culture dishes in growth factor supplemented methylcellulose medium. After 1 week of incubation at 37° C. in 5% $CO_2$, mix of CFU-Cs were enumerated under an inverted microscope. For chemotaxis assays, $1 \times 10^5$ Lin$^-$ cells were added to the upper chambers of a 24-well plate with 5 μm pore-size Transwell inserts (Millipore) containing or not different concentrations of Cxcl12 (R&D Systems) in lower chambers. Migrated cells were enumerated by CFU-Cs Mix assay after 4 hr of incubation at 37° C., 5% $CO_2$ and referred to input BM CFU-Cs to obtain a migration percentage. Cxcr4 internalization assay was performed as previously described (Balabanian et al., 2012) with some minor modifications. Briefly, $1 \times 10^7$ BM cells were incubated at 37° C. for 45 min with the indicated concentrations of Cxcl12 or Ccl2 (R&D Systems). The reaction was stopped by adding ice-cold RMPI and brief centrifugation at 4° C. After one wash in acidic glycine buffer (pH 4.3), levels of Cxcr4 membrane expression were determined by flow cytometry using the additional markers CD3, CD45R, Gr-1, CD11b, Ter119 and CD41 antigens. Background fluorescence was evaluated using the corresponding PE-conjugated immunoglobulin-isotype control Ab. Cxcr4 expression in stimulated cells was calculated as follows: (Cxcr4 geometric MFI of treated cells/Cxcr4 geometric MFI of unstimulated cells)× 100; 100% correspond to receptor expression at the surface of cells incubated in medium alone. For in vitro haematopoietic differentiation experiments, purified LSK SLAM or MPP cells were seeded at 450 cells into a 96-well tissue culture plate in DMEM medium supplemented with 10% FBS, 1% penicillin, and the following cytokines (5, 10 or 50 ng/mL): SCF, IL-3, IL-6, IL-7, and Flt3. Cells were cultured at 37° C. in a humidified atmosphere containing 5% CO2, and were harvested at the indicated intervals to analyze by flow cytometry differentiation and proliferation status (Ki-67 staining) of HSPCs.

Cell Cycle and Survival Assays

For cell cycle analyses, purified BM Lin$^-$ cells from WT and mutant mice were permeabilized and fixed according to the manufacturer's instructions with the FOXP3 permeabilization kit (Foxp3/Transcription Factor Staining Buffer Set), and then labelled with Ki-67 Ab (clone B56, mouse IgG1, BD Biosciences) and DAPI before flow cytometric analysis. For label-retaining assays (Wilson et al., 2008), mice were injected intraperitoneally with 180 μg BrdU (Sigma) and maintained on water containing 800 μg/ml BrdU and 1% glucose during 12 days. The BrdU pulse was followed by a 3-weeks chase period to detect by flow cytometry LRC activity by combining surface staining to define ST-HSCs with intracellular staining using the BrdU-FITC labeling kit following the manufacturer's instructions (BD Biosciences). Cyclin D3 was detected by flow cytometry in fixed and permeabilized BM cells using a Cycline D3 mAb (clone 1/Cyclin D3, mouse IgG2b, BD Biosciences) followed by a secondary rat anti-mouse IgG2b PE-conjugated Ab (R&D Systems) (Galloway et al., 2016). Apoptosis was measured using the Active Caspase-3-FITC apoptosis detection kit or the Annexin V Apoptosis Detection Kit I (BD Biosciences) followed by DAPI staining according to the manufacturer's instructions as described (Balabanian et al., 2012; Biajoux et al., 2016).

Flow-Cytometric Analyses

All Staining analyses were carried out on an LSRII Fortessa flow cytometer using the following mAbs: anti-mouse CD3 (clone 145-2C11, hamster IgG1), CD4 (clone RM4-5, rat IgG2a), CD8 (clone 53-6.7, rat IgG2a), CD11b (clone M1/70, rat IgG2b), CD16/32 (clone 93, rat IgG2a), CD21 (clone 7G6, rat IgG2b), CD25 (clone PC61, rat IgG1), CD34 (clone RAM34, rat IgG2a), CD41 (clone MWReg30, rat IgG1), CD43 (clone S7, rat IgG2a), CD44 (clone IM7, rat IgG2b), CD45R/B220 (clone RA3-6B2, rat IgG2a), CD45.1 (clone A20, mouse IgG2a), CD45.2 (clone 104, mouse IgG2a), CD48 (clone HM48-1, Armenian hamster IgG), CD62L (clone MEL-14, rat IgG2a), CD117 (clone 2B8, rat IgG2b), CD127 (clone A7R34, rat IgG2a), CD135 (clone A2F10, rat IgG2a), CD150 (clone TC15-23F12,2, rat IgG2a), Ter119 (clone TER-119, rat IgG2b), Gr-1 (clone RB6-8C5, rat IgG2b), Sca-1 (clone E13-161,7, rat IgG2a), IgM (clone II/41, ratIgG2a), and Cxcr4 (clone 2B11, rat IgG2b). Abs were conjugated to Biotin, BV 650, FITC, PE, APC, AF700, PE-Cyanin (Cy) 5, PE-Cy-Cy7, efluor 450, AF 647, APC-eFluor 780, peridinin chlorophyllprotein PerCP-Cy5,5 or pacific blue and purchased from BD Biosciences, eBioscience, Biolegend or Sony. The lineage Ab cocktail included anti-CD3, anti-CD45R, anti-CD11b, anti-TER119, anti-CD41 and anti-Gr-1 mAbs. Secondary labeling was performed with a Streptavidin-pacific orange from Life Technologies.

Immunofluorescence

Spleens were embedded in OCT medium (TissueTek). Cryosections (7 µm) were washed twice with PBS 1× and blocked in a solution of PBS BSA 5% for 1 hr. Sections were stained over night at 4° C. and for 1 h at room temperature with the following unconjugated Abs: polyclonal rabbit anti-mouse Cxcl12 (Thermofisher) and/or polyclonal goat anti-mouse Tcf21 (Santa Cruz). Sections were washed twice with PBS 1× and incubated with the appropriate secondary Ab (Invitrogen): anti-rabbit and/or anti-goat conjugated to AlexaFluor (AF) 594 or AF 488 for 30 min and 1 hr respectively at room temperature together with DAPI for nuclear staining. Mounting was done using Permafluor mounting medium (Thermo Scientific). Slides were scanned using a NanoZoomer Digital Pathology system 40× objective lens with numerical aperture 0.75 (Hamamatsu Photonic).

ELISA

Spleens were harvested and cell suspensions were filtered through a 70-µm nylon strainer and centrifuged at 1,500 rpm for 5 min. The supernatants were collected and analyzed using a standardized ELISA for murine Cxcl12 (Quantikine R&D Systems).

Quantitative Real Time (RT)-PCR

For Cxcl12 expression, total cellular RNA was isolated from spleen cells using the RNeasy Plus Mini Kit (Qiagen) and reverse transcribed with poly-d(T)-15 and Moloney murine leukemia virus reverse transcriptase (Fisher Bioblock). RNA was quantified using NanoDrop technology (Invitrogen). Amplification of cDNAs was performed by quantitative RT-PCR reactions on a Light Cycler instrument (LC480, Roche Diagnostics) with the LightCycler 480 SYBR Green detection kit (Roche Diagnostics) using the primers reported in Supplementary Table 1. The dissociation curve method was applied according to the manufacturer's protocol (60° C. to 95° C.) to ensure the presence of a single specific PCR product. Relative quantification was performed with the standard curve method, and results were expressed as Cxcl12/Gapdh ratios. For Cyclin expression, purified BM ST-HSCs were frozen at −80° C. during 5 min and then directly reverse transcribed with the SuperScript III Reverse Transcriptase (Invitrogen). Amplification of cDNAs was performed by quantitative RT-PCR reactions on a real-time PCR instrument (7500, Life Technologies-Applied Biosystems) with the TaqMan Universal PCR Master Mix (Applied Biosystems) using the following primers (Applied Biosystems): Ccnd1 (Mm00432359_m1), Ccnd2 (Mm00438070_m1), Ccnd3 (Mm01612362_m1) and β-actin (Mm01205647_g1). β-actin was used as the reference standard for normalization and relative quantification of fold-differences in mRNA expression was determined by the comparative delta-delta-ct ($2^{-\Delta\Delta CT}$) method. Fold changes were calculated by setting the mean values obtained from WT cells as one.

Statistics

Data are expressed as mean±SEM. All statistical analyses were conducted with the Prism software (GraphPad). A Kruskal-Wallis test was used to determine the significance of the difference between means of WT, +/1013 and 1013/1013 groups (#P<0.05, ##P<0.005 and ### P<0.0005). The unpaired two-tailed Student t test (for mice experiments) or the Mann-Whitney test (for human experiments) was used to compare means among two groups.

Results

The Reduction in Early B-/T-Cell Progenitors is Proportional to $Cxcr4^{1013}$ Allelic Dose To determine how the gain-of-Cxcr4-function mutation impacts on HSPC homeostasis (data not shown), global haematopoietic development was assessed in non-manipulated $Cxcr4^{+/+}$ (WT) and +/1013 mice. To avoid interference by the WT allele, we also analyzed homozygous $Cxcr4^{1013/1013}$ (1013/1013) mice. There was a profound lymphopenia in mutant mice that affects predominantly naive ($CD3^+$ $CD44^{-/low}CD62L^{high}$) T and immature ($B220^+$ $IgM^{high}CD21^{low}$) B cells and follows a $Cxcr4^{1013}$ allele dose-dependent pattern (data not shown). Red blood cell and platelet counts, hematocrit and hemoglobin levels did not differ between WT and mutant mice (data not shown). We next performed detailed immunophenotyping of early lymphoid progenitors in primary LOs. In the BM, 1013/1013 mice exhibited earlier and more severe defects in B-cell ontogeny than +/1013 mice, with reductions in both pro-B ($B220^+IgM^-CD43^+$) and pre-B ($B220^+IgM^-CD43^-$) cells (data not shown). We also observed a clear $Cxcr4^{1013}$ allele dose-dependent increase in the proportion of apoptotic pro-B and pre-B cells (data not shown). Numbers of developing T cells including DN1-DN4 thymocytes were also significantly reduced in a $Cxcr4^{1013}$ allele dose-dependent fashion (data not shown). Moreover, the number of early thymic progenitors (ETP), defined as $Lin^-CD4^-CD8^-c-Kit^+$ $CD44^{high}CD25$, was reduced in a $Cxcr4^{1013}$ allele dose-dependent manner (data not shown).

To determine whether the reduction in early B-/T-cell progenitors and the circulating lymphopenia result from a lymphocyte-intrinsic defect or an alteration of the LO microenvironment, BM reconstitution experiments were performed (data not shown). BM cells from WT, +/1013 or 1013/1013 $CD45.2^+$ mice were transplanted into lethally irradiated WT $CD45.1^+$ recipients. Four months after reconstitution, there were significantly lower numbers of T and B cells in the blood of $Cxcr4^{1013}$-bearing BM-chimeric mice compared to WT chimeras (data not shown). Pro-B cells were substantially decreased in the BM of 1013/1013 engrafted mice, while ETPs were decreased in the thymus of both $Cxcr4^{1013}$-bearing BM-chimeric mice (data not shown). We performed reverse chimeras in which $CD45.2^+$ WT and mutant mice were irradiated and reconstituted with WT $CD45.1^+$ BM (data not shown). The numbers of lymphocytes in peripheral blood, pro-B cells in BM and ETP in thymus were comparable in all groups (data not shown). There was a decrease in the number of $CD11b^+Gr-1^+$ myeloid cells in the blood of mutant mice that followed a $Cxcr4^{1013}$ allele dose-dependent pattern (data not shown). This was mirrored by an increase in myeloid cells in the BM (data not shown). Comparable findings were obtained in the blood and BM of $Cxcr4^{1013}$-bearing BM-chimeric mice compared to WT chimeras (data not shown). Reverse chimeras revealed no change in the number of myeloid cells in the blood and BM between all groups (data not shown). Thus, both the reduction in early T- and B-cell progenitors and the increase in mature myeloid cells in the BM of $Cxcr4^{1013}$-bearing mice result from a cell-intrinsic defect in Cxcr4-mediated signaling.

The Pool of $Cxcr4^{1013}$-Bearing Lymphoid-Committed Progenitors is Reduced in the BM HSCs generate mature leukocytes via a succession of increasingly committed downstream progenitor cells (Doulatov et al., 2012). Thus, we quantified the pool of lymphoid-primed multipotent (LMPP, LSK $Flt3^{high}CD34^+$) and common lymphoid (CLP, $Lin^-c-Kit^{low}Sca-1^{low}Flt3^+CD127^+$)

progenitors in the BM of WT and mutant mice (data not shown) (Ding and Morrison, 2013). There was a profound decrease in the number of LMPPs and CLPs in mutant mice (data not shown). BM chimeras were used to demonstrate that this decrease in lymphoid progenitors observed in Cxcr4$^{1013}$-bearing mice involved a cell-intrinsic defect (data not shown). This decline was not associated with changes in apoptosis of lymphoid progenitors (data not shown). In contrast to the reduction in LMPPs and CLPs, no changes in common myeloid (CMP, Lin$^-$c-Kit$^+$Sca-1$^-$CD34$^+$CD16/32$^-$), granulocyte-macrophage (GMP, Lin$^-$c-Kit$^+$Sca-1$^-$CD34$^+$CD16/32$^+$) and megakaryocyte-erythroid (MEP, Lin$^-$c-Kit$^+$Sca-1$^-$CD34$^-$CD16/32$^-$) progenitors could be detected (data not shown). These findings suggest a reduced capacity of Cxcr4$^{1013}$-bearing HSPCs to generate the earliest lymphoid progenitors, while leaving their apparent ability to produce myeloid progenitors intact.

Loss of Lymphoid Potential Occurs at the HSC-to-MPP Transition in Absence of Cxcr4 Desensitization In Vitro The major divergence of lymphoid and myeloid lineages occurs at the multipotent progenitor (MPP) stage (data not shown). To characterize the stage from which the lymphopoiesis process is impacted in mutant mice, we next assessed the pool of MPPs (Lin$^-$c-Kit$^+$Sca-1$^+$ [LSK] CD48$^-$CD150$^-$). Intriguingly, although the CMP pool was not affected in Cxcr4$^{1013}$-bearing mice, there was a Cxcr4$^{1013}$ allele dose-dependent decrease in the number of MPPs in mutant mice (data not shown). MPPs defined as LSK Flt3$^+$CD34$^+$ (Hidalgo et al., 2012) were also decreased in the BM of mutant mice (not shown). BM chimeras highlighted that this reduction in MPP numbers involved a cell-autonomous defect (data not shown). As the numbers of CMPs, GMPs and MEPs were normal in the BM of mutant mice, these data suggested that the pool of Cxcr4$^{1013}$-bearing MPPs is myeloid-biased, being profoundly depleted in lymphoid potential but still containing myeloid potential. Supporting this assumption, we observed increased frequency of myeloid-biased CD150$^{high}$ LSK CD34$^-$ cells in the BM of 1013/1013 mice (data not shown, Young et al., 2016).

LSK CD48$^-$CD150$^+$ (Signaling Lymphocyte Activation Molecule or SLAM) HSCs that encompass LSK Flt3$^-$CD34$^-$CD48$^-$CD150$^+$ (Long Term or LT) and LSK Flt3$^-$CD34$^+$CD48$^-$CD150$^+$ (Short Term or ST) subsets precede MPPs in the haematopoietic differentiation tree (data not shown). We hypothesized that the overall myeloid skewing of mutant HSCs contributes to the reduction in lymphoid potential of MPPs and consequently, in committed downstream lymphoid progenitors. To test this, we first quantified the number of MPPs that could be generated in vitro from WT and mutant LSK SLAM. Similar numbers of sorted LSK SLAM from the BM of WT and mutant mice were cultured for up to 4 days in feeder-free media in the presence of a set of cytokines (Nie et al., 2008; Tsai et al., 2013; Cho et al., 1999). Both frequencies and numbers of MPPs were slightly but significantly lower in Cxcr4$^{1013}$-bearing cell cultures compared to the WT ones over the course of the assay (data not shown). Second, we sought to determine whether Cxcr4$^{1013}$-carrying MPPs contained cells capable to differentiate into LMPPs. We found that Cxcr4$^{1013}$-bearing MPPs were less efficient at producing LMPPs by days 2 and 4 compared to WT cells (data not shown). The proliferation status did not differ between WT and mutant HSPCs (data not shown).

Finally, we examined in vitro the function of the Cxcl12/Cxcr4 axis in HSPCs. Membrane expression of Cxcr4 was similar between WT and mutant BM HSPCs (data not shown). However, +/1013 and 1013/1013 Lin$^-$ cells, which include HPSCs, displayed both impaired Cxcr4 internalization following Cxcl12 stimulation and increased Cxcl12-promoted chemotaxis (data not shown). Thus, the desensitization-resistant C-tail-truncated Cxcr4$^{1013}$ receptor is functionally expressed on HSPCs and leads to hypersensitivity to Cxcl12. These findings indicate that Cxcr4 desensitization regulates differentiation of HSCs into MPPs and further report a previously unanticipated role for such regulatory process in the MPP-to-LMPP transition.

Increased Quiescence of Cxcr4$^{1013}$-Bearing Short-Term HSCs in the BM

We next investigated the impact of the Cxcr4 mutation on BM HSC homeostasis. Compared to WT mice, mutant mice had normal numbers of LSK and LSK SLAM including both LT- and ST-HSC subpopulations (data not shown). Relevant functions of the Cxcl12/Cxcr4 signaling in HSC biology include regulating their quiescence (Nie et al., 2008; Tzeng et al., 2011). We observed a slight but significant increase in proportions of BM LSK SLAM cells in the quiescent G0 state (DAPI$^{low}$Ki-67$^-$) in mutant mice (data not shown). The latter was particularly evident in 1013/1013 ST-HSCs and spared the LT-HSC pool. We also examined the effect of intraperitoneal injection of 5-Fluorouracil (5-FU), which selectively eliminates cycling, but not quiescent HSCs. Following a single dose of 5-FU, we observed higher numbers of ST-HSCs in mutant mice that follow an allele dose-dependent fashion compared with WT controls (data not shown). We next evaluated how fast mutant ST-HSCs would divide by performing BrdU label-retaining cell (LRC) assays. Consistent with the DAPI/Ki-67 staining, we observed after a 12-days pulse period a Cxcr4$^{1013}$ allele dose-dependent reduction in BrdU incorporation within mutant ST-HSCs compared with WT ones (data not shown). After 3 weeks of chase, ST-HSCs carrying or not the Cxcr4 mutation had lost most of LRC activity. We also examined the expression levels of selected regulators of the cell cycle machinery by quantitative RT-PCR in ST-HSCs sorted from the BM of WT and mutant mice. We focused on expression of genes encoding D-type cyclins (D1-D3), which regulate G1-S transition notably in HSPCs and inversely correlate with CXCR4 expression (Nie et al., 2008; Tsai et al., 2013). Consistent with the increased quiescent status of mutant ST-HSCs, levels of D-cyclin mRNAs were significantly decreased in 1013/1013 ST-HSCs over control cells (data not shown). This was corroborated at the protein level as shown by flow-cytometry stains for Cyclin D3 (data not shown). Together, these findings reveal that the quiescence/cycling balance is disturbed in Cxcr4$^{1013}$-bearing BM ST-HSCs.

Impaired Homing, Multipotency and Self-Renewal Properties of Cxcr4$^{1013}$-Bearing HSCs Aforementioned findings suggest that Cxcr4$^{1013}$-bearing HSPCs exhibit impaired lymphoid capacity associated with a myeloid-bias, which together evoke an aging-induced shift in HSC composition (Young et al., 2016). In line with this, middle-aged (56-weeks old) WT mice displayed increased number of LT-HSCs (data not shown). Numbers of LSK SLAM were higher in the BM of mutant mice than in that of WT mice, proportional to Cxcr4$^{1013}$ allele dose. This was observed in both LT- and ST-HSC populations (data not shown). The proportions of LT- and ST-HSCs in the quiescent G0 state were slightly but significantly decreased in the BM of middle-aged mutant mice (data not shown). These results indicate that the desensitization-resistant Cxcr4$^{1013}$ receptor is associated with changes in the quiescence/cycling balance in Cxcr4$^{1013}$-bearing BM HSCs and their expansion with age. Serial BM transplantation is considered in many aspects as a stress setting (Karpova and Bonig, 2015), in which both the multipotency and self-renewal abilities of HSCs can be assessed in vivo. Primary engraftments were accomplished by transferring BM cells from young (8 to 12-weeks old) CD45.2$^+$ WT or mutant mice into lethally irradiated young CD45.1$^+$ WT recipients. Four months later, BMs from these chimeric mice were transferred into a second set of lethally irradiated young CD45.1$^+$ WT recipients. After primary reconstitution, there was a marked reduction in frequency and absolute number of CD45.2$^+$ LSK SLAM in the BM of CD45.1$^+$ WT recipients engrafted with 1013/1013 BM, but no defect in BM reconstitution using +/1013 HSCs (data not shown). In secondary transplantation, a dramatically reduced contribution of Cxcr4$^{1013}$-bearing CD45.2$^+$ HSCs to the BM of WT recipients highlighted the decreased capacity for self-renewal of these cells (data not shown). In reverse chimeras, the proportion and number of BM CD45.1$^+$ LSK and LSK SLAM cells were comparable between experimental groups (data not shown), indicating that impaired reconstitution capacity of 1013/1013 HSCs occurs in a cell-intrinsic manner. In vivo homing assays revealed a Cxcr4$^{1013}$ allele dose-dependent reduction in the BM homing potential of LSK and LSK SLAM (data not shown). Collectively these findings show that the in vivo homing potential of Cxcr4$^{1013}$-bearing HSCs is impaired, indicating that efficient Cxcr4 desensitization is required for BM engraftment and reconstitution.

Abnormal Distribution of Cxcr4$^{1013}$-Bearing HSPCs in the Periphery

The Cxcl12/Cxcr4 pair regulates HSPC retention in and egress from the BM (Foudi et al., 2006; Christopher et al., 2009; Broxmeyer et al., 2005; Nie et al., 2008). We explored whether the Cxcr4 mutation affected the peripheral distribution of HSPCs. We found that the number of CFU-Cs in blood of mutant mice was decreased in a Cxcr4$^{1013}$ allele dose-dependent fashion (data not shown). A similar phenomenon was observed in blood samples drawn from two unrelated and two related patients with WS and carrying distinct autosomal dominant mutations in CXCR4. There were significant reductions in the number of CFU-Cs, HSCs/MPPs (defined as CD45RA$^-$CD38$^-$CD34$^+$) and immature multi-lymphoid progenitors (MLPs, defined as CD45RA$^+$CD38$^-$CD7$^-$CD34$^+$CD10$^+$) in the circulation of patients compared with healthy individuals (data not shown). This pattern of HSPC dysfunctions was extended to the blood of a WHIM$^{WT}$ patient that was reported to display impaired CXCR4 desensitization to CXCL12 (Balabanian et al., 2005, 2008). These findings suggest an abnormal recirculation of mutant HSPCs in both mice and humans.

To determine the role of the Cxcr4 mutation in a stressed mobilization situation, we assessed the impact of a single intra-peritoneal injection of the Cxcr4 antagonist AMD3100 on HSPC distribution in the blood of WT and mutant mice. One hour after injection, AMD3100-mediated inhibition of Cxcr4 signaling in WT mice led to a significant increase in the absolute numbers of circulating HSPCs (data not shown). Mutant HSPCs were also sensitive to haematopoietic insults as AMD3100 treatment increased their absolute numbers in the blood, reaching that observed in untreated WT mice. Thus, enforced mobilization of HSPCs with AMD3100 was apparently normal in mice carrying desensitization-resistant Cxcr4 receptors.

We next sought to determine the representation of Cxcr4$^{1013}$-bearing HSPCs in the spleen, where haematopoiesis can expand under specific settings, a process referred to as extramedullary haematopoiesis (EMH) (Baldridge et al., 2010; Wolf and Neiman, 1987; Morrison et al., 1997). We observed that mutant mice displayed significantly increased frequencies and numbers of splenic LSK SLAM in a Cxcr4$^{1013}$ allele dose-dependent fashion (data not shown). Moreover, 1013/1013 spleens also had significantly increased numbers of CFU-Cs, CMPs and GMPs compared to WT, while MEPs remained unchanged (data not shown). The substantial increase in splenic HSCs and subsets of myeloid-committed progenitors observed in young adult mutant mice compared to WT was even more pronounced in middle-aged mice, affecting CFU-Cs, CMPs, GMPs and MEPs (data not shown). In vivo homing assays revealed increased numbers of Lin$^-$ cells recovered from the spleens of WT CD45.1$^+$ recipients injected with mutant CD45.2$^+$ BM cells (data not shown). This suggests that enhancement of EMH might be a consequence of increased homing of Cxcr4$^{1013}$-bearing HSPCs from circulation to spleen. Similar to full mice (data not shown), the numbers of splenic LSK SLAM, CMPs and GMPs were increased in Cxcr4$^{1013}$-carrying BM chimeras compared to WT chimeras (data not shown). In reverse chimeras, the numbers of splenic LSK SLAM were comparable in all experimental groups, whereas myeloid progenitors were increased in the spleen of 1013/1013 recipients (data not shown). These results indicate that the expansion of LSK SLAM is predominantly intrinsic to the gain-of-Cxcr4-function in HSCs, while that of the myeloid progenitors involves both intrinsic and extrinsic defects.

Splenic EMH is Associated with Increased Detection of Cxcl12 in Cxcr4$^{1013}$-Bearing Mice During splenic EMH, HSCs predominantly localize around sinusoids in the red pulp, where Cxcl12 is expressed by sinusoidal endothelial cells in humans and a subset of perivascular stromal cells in mice (Miwa et al., 2013; Inra et al., 2015). Notably, EMH induction in mice was found to expand stromal cells by promoting their proliferation (Inra et al., 2015). Thus, we examined the Cxcl12 status in the spleen of adult Cxcr4$^{1013}$-bearing mice, where enhanced EMH develops under steady-state conditions. By quantitative real-time PCR, we found that transcripts encoding Cxcl12 were detectable at similar level in the spleens of both WT and Cxcr4$^{1013}$-bearing mice (data not shown). However, the Cxcl12 protein was significantly increased in spleen supernatants from 1013/1013 mice (data not shown). This would be consistent with increased Cxcl12 production by an expanded but still numerically small population of stromal cells in adult spleen of Cxcr4$^{1013}$-bearing mice. Thus, we performed immunostainings on splenic sections from WT and mutant mice to better delineate the source of Cxcl12. Cxcl12 staining was significantly stronger in mutants than in WT spleens in a Cxcr4$^{1013}$ allele dose-dependent manner (data not shown). Consistent with previous reports (Inra et al., 2015; Miwa et al., 2013; Wang et al., 2015), Cxcl12 was primarily detected in the red pulp, although some white pulp central arterioles also stained positive. Tcf21-positive perivascular stromal cells were markedly expanded in the spleens of mutant mice and further identified as a source of Cxcl12 in the red pulp (data not shown). Thus, increased Cxcl12 in the spleen of Cxcr4$^{1013}$-bearing mice was observed in the setting of an abnormal expansion of Tcf21$^+$ stromal cells during EMH.

Example 2: New In Vitro Differentiation Assay

Material & Methods

Purified LSK SLAM (HSCs) or MPPs were seeded at 450 cells into a 96-well tissue culture plate in DMEM medium supplemented with 10% FBS, 1% penicillin, and the following cytokines: mouse SCF (50 ng/mL), mouse IL-3 (10 ng/mL), human IL-6 (10 ng/mL), mouse IL-7 (5 ng/mL), and human Flt3 (5 ng/mL). 100 ng/mL CXCL12 was added or not at the start of the culture. Cells were cultured at 37° C. in a humidified atmosphere containing 5% CO2, and were harvested at the indicated intervals to analyze HSPCs by flow cytometry.

Results

The inventors recently carried out an original in vitro differentiation assay. Briefly, in a mouse model of the WS, $Cxcr4^{1013}$-bearing ST-HSCs, which precede MPPs in the haematopoietic differentiation tree, are more quiescent and this could contribute, at least in part, to the in vivo reduction in MPPs and committed downstream lymphoid progenitors (i.e. LMPPs and CLPs). Thus, they have compared in vitro the potential of LSK SLAM from WT and mutant (+/1013 and 1013/1013) mice to differentiate into the non self-renewing MPP subset. To this end, they have set up a feeder-free media including the presence of required cytokines (mSCF, mIL-3, hIL-6, mIL-7 and hFlt3) in which similar numbers of sorted LSK SLAM from the BM of WT and mutant mice were cultured for up to 7 days. At day 2, the numbers of WT LSK SLAM and MPPs were comparable and at day 4 the number of LSK SLAM dropped considerably whereas that of MPPs rose, indicating efficient differentiation of presumably ST-HSCs into MPPs over time. This successful differentiation assay including the expected altered capacity of $Cxcr4^{1013}$-bearing ST-HSCs to give rise to MPPs represents a proof of concept study, on which they are trying to build in vitro conditions permissive for lymphoid differentiation of MPPs. Indeed, they next evaluated the ability of similar numbers of sorted MPPs from the BM of WT and mutant mice to differentiate into LMPPs. Their experiments revealed that $Cxcr4^{1013}$-bearing MPPs were less efficient at producing LMPPs by days 2 and 4 compared to WT cells. This suggests that mutant MPPs appear to be not able to differentiate correctly in LMPPs in vitro, potentially providing an explanation for the marked reduction in LMPPs observed in the BM of mutant mice in vivo. Surprisingly, addition of the chemokine CXCL12 at the start of the assay further enhanced both proportions and numbers of $Cxcr4^{1013}$-bearing MPPs and promoted the appearance of LMPPs regardless of the Cxcr4 genotype, although this effect was less pronounced among mutant cells. This might rely on a pro-lymphoid effect of CXCL12 on MPPs and their choice to differentiate into downstream lymphoid-committed progenitors (FIGS. 1 and 2). Interestingly, this transition appears to be partly defective in mutant mice in vivo. These findings could constitute a strong lead for modeling a three- or four-dimensional co-culture system by inoculating MPPs into a bio-engineered niche.

Example 3: Impact of CXCL12 on Lymphoid Commitment of HSPCs

Material & Methods

Purified MPPs were seeded at 450 cells into a 96-well tissue culture plate in DMEM medium supplemented with 10% FBS, 1% penicillin, and the following cytokines: mouse SCF (50 ng/mL), mouse IL-3 (10 ng/mL), human IL-6 (10 ng/mL), mouse IL-7 (5 ng/mL), and human Flt3 (5 ng/mL). Different concentrations of CXCL12 ranging from 1 to 1,000 ng/ml were added at the start of the culture. Cells were cultured at 37° C. in a humidified atmosphere containing 5% CO2, and were harvested after 4 days of culture to analyze HSPCs by flow cytometry.

Results

CLPs and common myeloid progenitors (CMPs) are generated from phenotypically and functionally distinct subpopulations of lineage-biased MPPs, i.e. MPP2 and MPP3 are reported as distinct myeloid-biased MPP subsets that operate together with lymphoid-primed MPP4 to control blood leukocyte production. Thus, based on the aforementioned in vitro differentiation assay, the inventors have analyzed the impact of different concentrations of CXCL12 on the fate of HSPCs. Addition of CXCL12 at the start of the assay resulted by day 4 in a significant and dose-dependent increase in proportions and absolute numbers of MPPs and lymphoid-biased MPP4 (FIG. 3). This was mirrored by a decrease in myeloid-biased MPP2 and MPP3 proportions and numbers. Such output supports a critical role for CXCL12 in regulating the lymphoid-myeloid specification of HSPCs. Notably, this relies on the pro-lymphoid effect of CXCL12 on MPP4, also referred as LMPP (see examples 1 and 2), and their choice to differentiate into downstream lymphoid progenitors.

REFERENCES

Throughout this application, various references describe the state of the art to which this invention pertains. The disclosures of these references are hereby incorporated by reference into the present disclosure.

Balabanian, K., E. Brotin, V. Biajoux, L. Bouchet-Delbos, E. Lainey, O. Fenneteau, D. Bonnet, L. Fiette, D. Emilie, and F. Bachelerie. 2012. Proper desensitization of CXCR4 is required for lymphocyte development and peripheral compartmentalization in mice. Blood. 119:5722-5730. doi:10.1182/blood-2012-01-403378.

Balabanian, K., B. Lagane, J. L. Pablos, L. Laurent, T. Planchenault, O. Verola, C. Lebbe, D. Kerob, A. Dupuy, O. Hermine, J.-F. Nicolas, V. Latger-Cannard, D. Bensoussan, P. Bordigoni, F. Baleux, F. Le Deist, J.-L. Virelizier, F. Arenzana-Seisdedos, and F. Bachelerie. 2005. WHIM syndromes with different genetic anomalies are accounted for by impaired CXCR4 desensitization to CXCL12. Blood. 105:2449-2457. doi:10.1182/blood-2004-06-2289.

Baldridge, M. T., K. Y. King, N.C. Boles, D. C. Weksberg, and M. A. Goodell. 2010. Quiescent haematopoietic stem cells are activated by IFN-gamma in response to chronic infection. Nature. 465:793-797. doi:10.1038/nature09135.

Beaussant Cohen, S., O. Fenneteau, E. Plouvier, P.-S. Rohrlich, G. Daltroff, I. Plantier, A. Dupuy, D. Kerob, B. Beaupain, P. Bordigoni, F. Fouyssac, A.-L. Delezoide, G. Devouassoux, J. F. Nicolas, P. Bensaid, Y. Bertrand, K. Balabanian, C. B. Chantelot, F. Bachelerie, and J. Donadieu. 2012. Description and outcome of a cohort of 8 patients with WHIM syndrome from the French Severe Chronic Neutropenia Registry. Orphanet J. Rare Dis. 7:71. doi:10.1186/1750-1172-7-71.

Broxmeyer, H. E., C. M. Orschell, D. W. Clapp, G. Hangoc, S. Cooper, P. A. Plett, W. C. Liles, X. Li, B. Graham-Evans, T. B. Campbell, G. Calandra, G. Bridger, D. C. Dale, and E. F. Srour. 2005. Rapid mobilization of murine and human hematopoietic stem and progenitor cells with AMD3100, a CXCR4 antagonist. J. Exp. Med. 201:1307-1318. doi:10.1084/jem.20041385.

Cabezas-Wallscheid, N., D. Klimmeck, J. Hansson, D. B. Lipka, A. Reyes, Q. Wang, D. Weichenhan, A. Lier, L. von Paleske, S. Renders, P. Wünsche, P. Zeisberger, D. Brocks, L. Gu, C. Herrmann, S. Haas, M. A. G. Essers, B.

Brors, R. Eils, W. Huber, M. D. Milsom, C. Plass, J. Krijgsveld, and A. Trumpp. 2014. Identification of regulatory networks in HSCs and their immediate progeny via integrated proteome, transcriptome, and DNA methylome analysis. Cell Stem Cell. 15:507-522. doi:10.1016/j.stem.2014.07.005.

Cheng, T., N. Rodrigues, H. Shen, Y. Yang, D. Dombkowski, M. Sykes, and D. T. Scadden. 2000. Hematopoietic stem cell quiescence maintained by p21cip1/waf1. Science. 287:1804-1808.

Chen, Z., X. Pan, Y. Yao, F. Yan, L. Chen, R. Huang, and G. Ma. 2013. Epigenetic regulation of cardiac progenitor cells marker c-kit by stromal cell derived factor-1α. PloS One. 8:e69134. doi:10.1371/journal.pone.0069134.

Cho, S. K., T. D. Webber, J. R. Carlyle, T. Nakano, S. M. Lewis, and J. C. Zúñiga-Pflücker. 1999. Functional characterization of B lymphocytes generated in vitro from embryonic stem cells. Proc. Natl. Acad. Sci. U.S.A. 96:9797-9802.

Christopher, M. J., F. Liu, M. J. Hilton, F. Long, and D. C. Link. 2009. Suppression of CXCL12 production by bone marrow osteoblasts is a common and critical pathway for cytokine-induced mobilization. Blood. 114:1331-1339. doi:10.1182/blood-2008-10-184754.

Cordeiro Gomes A, Hara T, Lim V Y, Herndler-Brandstetter D, Nevius E, Sugiyama T4, Tani-Ichi S, Schlenner S, Richie E, Rodewald H R, Flavell R A, Nagasawa T, Ikuta K, Pereira J P. Hematopoietic Stem Cell Niches Produce Lineage-Instructive Signals to Control Multipotent Progenitor Differentiation. Immunity. 2016 Dec. 20; 45(6):1219-1231. doi: 10.1016/j.immuni.2016.11.004. Epub 2016 Nov. 29.

Ding, L., and S. J. Morrison. 2013. Haematopoietic stem cells and early lymphoid progenitors occupy distinct bone marrow niches. Nature. 495:231-235. doi:10.1038/nature11885.

Dotta, L., L. Tassone, and R. Badolato. 2011. Clinical and genetic features of Warts, Hypogammaglobulinemia, Infections and Myelokathexis (WHIM) syndrome. Curr. Mol. Med. 11:317-325.

Doulatov, S., F. Notta, E. Laurenti, and J. E. Dick. 2012. Hematopoiesis: a human perspective. Cell Stem Cell. 10:120-136. doi:10.1016/j.stem.2012.01.006.

Eash, K. J., A. M. Greenbaum, P. K. Gopalan, and D. C. Link. 2010. CXCR2 and CXCR4 antagonistically regulate neutrophil trafficking from murine bone marrow. J. Clin. Invest. 120:2423-2431. doi:10.1172/JCI41649.

Foudi, A., P. Jarrier, Y. Zhang, M. Wittner, J.-F. Geay, Y. Lecluse, T. Nagasawa, W. Vainchenker, and F. Louache. 2006. Reduced retention of radioprotective hematopoietic cells within the bone marrow microenvironment in CXCR4-/- chimeric mice. Blood. 107:2243-2251. doi:10.1182/blood-2005-02-0581.

Gautreau, L., A. Boudil, V. Pasqualetto, L. Skhiri, L. Grandin, M. Monteiro, J.-P. Jais, and S. Ezine. 2010. Gene coexpression analysis in single cells indicates lymphomyeloid copriming in short-term hematopoietic stem cells and multipotent progenitors. J. Immunol. Baltim. Md. 1950. 184:4907-4917. doi:10.4049/jimmunol.0902184.

Gulino, A. V., D. Moratto, S. Sozzani, P. Cavadini, K. Otero, L. Tassone, L. Imberti, S. Pirovano, L. D. Notarangelo, R. Soresina, E. Mazzolari, D. L. Nelson, L. D. Notarangelo, and R. Badolato. 2004. Altered leukocyte response to CXCL12 in patients with warts hypogammaglobulinemia, infections, myelokathexis (WHIM) syndrome. Blood. 104:444-452. doi:10.1182/blood-2003-10-3532.

de Haan, G., W. Nijhof, and G. Van Zant. 1997. Mouse strain-dependent changes in frequency and proliferation of hematopoietic stem cells during aging: correlation between lifespan and cycling activity. Blood. 89:1543-1550.

Hernandez, P. A., R. J. Gorlin, J. N. Lukens, S. Taniuchi, J. Bohinjec, F. Francois, M. E. Klotman, and G. A. Diaz. 2003. Mutations in the chemokine receptor gene CXCR4 are associated with WHIM syndrome, a combined immunodeficiency disease. Nat. Genet. 34:70-74. doi:10.1038/ng1149.

Hidalgo, I., A. Herrera-Merchan, J. M. Ligos, L. Carramolino, J. Nuñez, F. Martinez, O. Dominguez, M. Torres, and S. Gonzalez. 2012. Ezh1 is required for hematopoietic stem cell maintenance and prevents senescence-like cell cycle arrest. Cell Stem Cell. 11:649-662. doi:10.1016/j.stem.2012.08.001.

Hock, H., M. J. Hamblen, H. M. Rooke, J. W. Schindler, S. Saleque, Y. Fujiwara, and S. H. Orkin. 2004. Gfi-1 restricts proliferation and preserves functional integrity of haematopoietic stem cells. Nature. 431:1002-1007. doi: 10.1038/nature02994.

Inra, C. N., B. O. Zhou, M. Acar, M. M. Murphy, J. Richardson, Z. Zhao, and S. J. Morrison. 2015. A perisinusoidal niche for extramedullary haematopoiesis in the spleen. Nature. 527:466-471. doi:10.1038/nature15530.

Itkin, T., S. Gur-Cohen, J. A. Spencer, A. Schajnovitz, S. K. Ramasamy, A. P. Kusumbe, G. Ledergor, Y. Jung, I. Milo, M. G. Poulos, A. Kalinkovich, A. Ludin, O. Kollet, G. Shakhar, J. M. Butler, S. Rafii, R. H. Adams, D. T. Scadden, C. P. Lin, and T. Lapidot. 2016. Distinct bone marrow blood vessels differentially regulate haematopoiesis. Nature. 532:323-328. doi:10.1038/nature17624.

Ito, K., A. Hirao, F. Arai, K. Takubo, S. Matsuoka, K. Miyamoto, M. Ohmura, K. Naka, K. Hosokawa, Y. Ikeda, and T. Suda. 2006. Reactive oxygen species act through p38 MAPK to limit the lifespan of hematopoietic stem cells. Nat. Med. 12:446-451. doi:10.1038/nm1388.

Karpova, D., and H. Bonig. 2015. Concise Review: CXCR4/CXCL12 Signaling in Immature Hematopoiesis—Lessons From Pharmacological and Genetic Models. Stem Cells Dayt. Ohio. 33:2391-2399. doi:10.1002/stem.2054.

Kawabata, K., M. Ujikawa, T. Egawa, H. Kawamoto, K. Tachibana, H. Iizasa, Y. Katsura, T. Kishimoto, and T. Nagasawa. 1999. A cell-autonomous requirement for CXCR4 in long-term lymphoid and myeloid reconstitution. Proc. Natl. Acad. Sci. U.S.A. 96:5663-5667.

Kawai, T., U. Choi, L. Cardwell, S. S. DeRavin, N. Naumann, N. L. Whiting-Theobald, G. F. Linton, J. Moon, P. M. Murphy, and H. L. Malech. 2007. WHIM syndrome myelokathexis reproduced in the NOD/SCID mouse xenotransplant model engrafted with healthy human stem cells transduced with C-terminus-truncated CXCR4. Blood. 109:78-84. doi:10.1182/blood-2006-05-025296.

Kawai, T., and H. L. Malech. 2009. WHIM syndrome: congenital immune deficiency disease. Curr. Opin. Hematol. 16:20-26. doi:10.1097/MOH.0b013e32831ac557.

Kozar, K., M. A. Ciemerych, V. I. Rebel, H. Shigematsu, A. Zagozdzon, E. Sicinska, Y. Geng, Q. Yu, S. Bhattacharya, R. T. Bronson, K. Akashi, and P. Sicinski. 2004. Mouse development and cell proliferation in the absence of D-cyclins. Cell. 118:477-491. doi: 10.1016/j.cell.2004.07.025.

Kriván, G., M. Erdos, K. Kállay, G. Benyó, A. Tóth, J. Sinkó, V. Goda, B. Tóth, and L. Maródi. 2010. Successful umbilical cord blood stem cell transplantation in a child with WHIM syndrome. Eur. J. Haematol. 84:274-275. doi:10.1111/j.1600-0609.2009.01368.x.

Lai, C.-Y., S. Yamazaki, M. Okabe, S. Suzuki, Y. Maeyama, Y. Iimura, M. Onodera, S. Kakuta, Y. Iwakura, M. Nojima, M. Otsu, and H. Nakauchi. 2014. Stage-specific roles for CXCR4 signaling in murine hematopoietic stem/progenitor cells in the process of bone marrow repopulation. Stem Cells Dayt. Ohio. 32:1929-1942. doi:10.1002/stem.1670.

Lipka, D. B., Q. Wang, N. Cabezas-Wallscheid, D. Klimmeck, D. Weichenhan, C. Herrmann, A. Lier, D. Brocks, L. von Paleske, S. Renders, P. Wiinsche, P. Zeisberger, L. Gu, S. Haas, M. A. Essers, B. Brors, R. Eils, A. Trumpp, M. D. Milsom, and C. Plass. 2014. Identification of DNA methylation changes at cis-regulatory elements during early steps of HSC differentiation using tagmentation-based whole genome bisulfite sequencing. Cell Cycle Georget. Tex. 13:3476-3487. doi:10.4161/15384101.2014.973334.

Ma, Q., D. Jones, P. R. Borghesani, R. A. Segal, T. Nagasawa, T. Kishimoto, R. T. Bronson, and T. A. Springer. 1998. Impaired B-lymphopoiesis, myelopoiesis, and derailed cerebellar neuron migration in CXCR4- and SDF-1-deficient mice. Proc. Natl. Acad. Sci. U.S.A. 95:9448-9453.

McDermott, D. H., J.-L. Gao, Q. Liu, M. Siwicki, C. Martens, P. Jacobs, D. Velez, E. Yim, C. R. Bryke, N. Hsu, Z. Dai, M. M. Marquesen, E. Stregevsky, N. Kwatemaa, N. Theobald, D. A. Long Priel, S. Pittaluga, M. A. Raffeld, K. R. Calvo, I. Maric, R. Desmond, K. L. Holmes, D. B. Kuhns, K. Balabanian, F. Bachelerie, S. F. Porcella, H. L. Malech, and P. M. Murphy. 2015. Chromothriptic cure of WHIM syndrome. Cell. 160:686-699. doi:10.1016/j.cell.2015.01.014.

Miwa, Y., T. Hayashi, S. Suzuki, S. Abe, I. Onishi, S. Kirimura, M. Kitagawa, and M. Kurata. 2013. Up-regulated expression of CXCL12 in human spleens with extramedullary haematopoiesis. Pathology (Phila.). 45:408-416. doi:10.1097/PAT.0b013e3283613dbf.

Morrison, S. J., D. E. Wright, and I. L. Weissman. 1997. Cyclophosphamide/granulocyte colony-stimulating factor induces hematopoietic stem cells to proliferate prior to mobilization. Proc. Natl. Acad. Sci. U.S.A. 94:1908-1913.

Nagasawa, T., S. Hirota, K. Tachibana, N. Takakura, S. Nishikawa, Y. Kitamura, N. Yoshida, H. Kikutani, and T. Kishimoto. 1996. Defects of B-cell lymphopoiesis and bone-marrow myelopoiesis in mice lacking the CXC chemokine PBSF/SDF-1. Nature. 382:635-638. doi:10.1038/382635a0.

Nagasawa, T., K. Tachibana, and T. Kishimoto. 1998. A novel CXC chemokine PBSF/SDF-1 and its receptor CXCR4: their functions in development, hematopoiesis and HIV infection. Semin. Immunol. 10:179-185. doi:10.1006/smim.1998.0128.

Nie, Y., Y.-C. Han, and Y.-R. Zou. 2008. CXCR4 is required for the quiescence of primitive hematopoietic cells. J. Exp. Med. 205:777-783. doi:10.1084/jem.20072513.

Onai, N., Y. y Zhang, H. Yoneyama, T. Kitamura, S. Ishikawa, and K. Matsushima. 2000. Impairment of lymphopoiesis and myelopoiesis in mice reconstituted with bone marrow-hematopoietic progenitor cells expressing SDF-1-intrakine. Blood. 96:2074-2080.

Orford, K. W., and D. T. Scadden. 2008. Deconstructing stem cell self-renewal: genetic insights into cell-cycle regulation. Nat. Rev. Genet. 9:115-128. doi:10.1038/nrg2269.

Peled, A., I. Petit, O. Kollet, M. Magid, T. Ponomaryov, T. Byk, A. Nagler, H. Ben-Hur, A. Many, L. Shultz, O. Lider, R. Alon, D. Zipori, and T. Lapidot. 1999. Dependence of human stem cell engraftment and repopulation of NOD/SCID mice on CXCR4. Science. 283:845-848.

Pietras, E. M., D. Reynaud, Y. A. Kang, D. Carlin, F. J. Calero-Nieto, A. D. Leavitt, J. M. Stuart, B. Göttgens and E. Passegué. 2015. Functionally Distinct Subsets of Lineage-Biased Multipotent Progenitors Control Blood Production in Normal and Regenerative Conditions. Cell Stem Cell. 17(1):35-46. doi:10.1016/j.stem.2015.05.003.

Pitt, L. A., A. N. Tikhonova, H. Hu, T. Trimarchi, B. King, Y. Gong, M. Sanchez-Martin, A. Tsirigos, D. R. Littman, A. A. Fernando, S. J. Morrison, D. R. Fooksman, I. Aifantis, and S. R. Schwab. 2015. CXCL12-Producing Vascular Endothelial Niches Control Acute T Cell Leukemia Maintenance. Cancer Cell. 27:755-768. doi:10.1016/j.ccell.2015.05.002.

Rossi, D. J., D. Bryder, J. M. Zahn, H. Ahlenius, R. Sonu, A. J. Wagers, and I. L. Weissman. 2005. Cell intrinsic alterations underlie hematopoietic stem cell aging. Proc. Natl. Acad. Sci. U.S.A. 102:9194-9199. doi:10.1073/pnas.0503280102.

Scimone, M. L., T. W. Felbinger, I. B. Mazo, J. V. Stein, U. H. Von Andrian, and W. Weninger. 2004. CXCL12 mediates CCR7-independent homing of central memory cells, but not naive T cells, in peripheral lymph nodes. J. Exp. Med. 199:1113-1120. doi:10.1084/jem.20031645.

Shao, L., H. Li, S. K. Pazhanisamy, A. Meng, Y. Wang, and D. Zhou. 2011. Reactive oxygen species and hematopoietic stem cell senescence. Int. J. Hematol. 94:24-32. doi:10.1007/s12185-011-0872-1.

Sugiyama, T., H. Kohara, M. Noda, and T. Nagasawa. 2006. Maintenance of the hematopoietic stem cell pool by CXCL12-CXCR4 chemokine signaling in bone marrow stromal cell niches. Immunity. 25:977-988.

Trampont, P. C., A.-C. Tosello-Trampont, Y. Shen, A. K. Duley, A. E. Sutherland, T. P. Bender, D. R. Littman, and K. S. Ravichandran. 2010. CXCR4 acts as a costimulator during thymic beta-selection. Nat. Immunol. 11:162-170. doi:10.1038/ni.1830.

Tsai, J. J., J. A. Dudakov, K. Takahashi, J.-H. Shieh, E. Velardi, A. M. Holland, N. V. Singer, M. L. West, O. M. Smith, L. F. Young, Y. Shono, A. Ghosh, A. M. Hanash, H. T. Tran, M. A. S. Moore, and M. R. M. van den Brink. 2013. Nrf2 regulates haematopoietic stem cell function. Nat. Cell Biol. 15:309-316. doi:10.1038/ncb2699.

Tzeng, Y.-S., H. Li, Y.-L. Kang, W.-C. Chen, W.-C. Cheng, and D.-M. Lai. 2011. Loss of Cxcl12/Sdf-1 in adult mice decreases the quiescent state of hematopoietic stem/progenitor cells and alters the pattern of hematopoietic regeneration after myelosuppression. Blood. 117:429-439. doi:10.1182/blood-2010-01-266833.

Wang, X., S. Y. Cho, C. S. Hu, D. Chen, J. Roboz, and R. Hoffman. 2015. C—X—C motif chemokine 12 influences the development of extramedullary hematopoiesis in the spleens of myelofibrosis patients. Exp. Hematol. 43:100-109.el. doi:10.1016/j.exphem.2014.10.013.

Wolf, B. C., and R. S. Neiman. 1987. Hypothesis: splenic filtration and the pathogenesis of extramedullary hematopoiesis in agnogenic myeloid metaplasia. Hematol. Pathol. 1:77-80.

Yahata, T., T. Takanashi, Y. Muguruma, A. A. Ibrahim, H. Matsuzawa, T. Uno, Y. Sheng, M. Onizuka, M. Ito, S. Kato, and K. Ando. 2011. Accumulation of oxidative DNA damage restricts the self-renewal capacity of human hematopoietic stem cells. Blood. 118:2941-2950. doi: 10.1182/blood-2011-01-330050.

Young K, Borikar S, Bell R, Kuffler L, Philip V, Trowbridge J J. Progressive alterations in multipotent hematopoietic progenitors underlie lymphoid cell loss in aging. J Exp Med. 2016 Oct. 17; 213(11):2259-2267. Epub 2016 Oct. 10.

Zhang, Y., A. Foudi, J.-F. Geay, M. Berthebaud, D. Buet, P. Jarrier, A. Jalil, W. Vainchenker, and F. Louache. 2004. Intracellular localization and constitutive endocytosis of CXCR4 in human CD34+ hematopoietic progenitor cells. Stem Cells Dayt. Ohio. 22:1015-1029. doi:10.1634/stemcells.22-6-1015.

The invention claimed is:

1. A method of differentiating hematopoietic stem and progenitor cells (HSPCs) into lymphoid progenitor cells, said method comprising
culturing the HSPCs in vitro in a culture medium comprising a cocktail of cytokines consisting of SCF, IL-3, IL-6, IL-7 and Flt-3, wherein the cytokines are present in an amount sufficient to cause differentiation of the HSPCs into lymphoid progenitor cells.

2. A method of differentiating hematopoietic stem and progenitor cells (HSPCs) into lymphoid progenitor cells, said method comprising
culturing the HSPCs in vitro in a culture medium comprising
a cocktail of cytokines consisting of SCF, IL-3, IL-6, IL-7 and Flt-3, and
chemokine CXCL12,
wherein the cytokines and the chemokine CXCL12 are present in an amount sufficient to cause differentiation of the HSPCs into lymphoid progenitor cells.

* * * * *